(12) United States Patent
Hunter, Jr.

(10) Patent No.: US 9,408,768 B1
(45) Date of Patent: *Aug. 9, 2016

(54) ARM STABILIZER FOR ELBOW SURGICAL PROCEDURE

(76) Inventor: Alton Lee Hunter, Jr., Columbia, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/558,213

(22) Filed: Jul. 25, 2012

Related U.S. Application Data

(63) Continuation of application No. 12/550,701, filed on Aug. 31, 2009, now Pat. No. 8,230,864.

(51) Int. Cl.
*A61G 13/12* (2006.01)

(52) U.S. Cl.
CPC ..................................... *A61G 13/12* (2013.01)

(58) Field of Classification Search
USPC .......... 128/845–846, 877–879; 602/20–23, 5, 602/13, 36; 600/485, 490, 500; 5/623–624, 5/648, 646, 650–651, 658
See application file for complete search history.

(56) References Cited

U.S. PATENT DOCUMENTS

| | | | |
|---|---|---|---|
| 473,200 A | 4/1892 | Streeter | |
| 5,537,702 A * | 7/1996 | Brown-Milants et al. | 5/632 |
| 5,785,057 A | 7/1998 | Fischer | |
| 5,884,974 A * | 3/1999 | Bergsten et al. | 297/411.35 |
| 5,904,655 A | 5/1999 | Brackett | |
| 5,961,512 A * | 10/1999 | Purnell | 606/1 |
| 7,017,215 B1 | 3/2006 | Singer et al. | |
| 7,143,458 B2 | 12/2006 | Slater, Jr. | |
| 7,441,293 B1 | 10/2008 | Singer et al. | |
| 8,230,864 B2 * | 7/2012 | Hunter, Jr. | 128/845 |
| 8,273,043 B2 * | 9/2012 | Bonutti | A61F 5/013 602/23 |
| 8,356,601 B2 | 1/2013 | Hunter, Jr. | |
| 2002/0128577 A1 * | 9/2002 | Smart | 602/36 |
| 2005/0251076 A1 | 11/2005 | Branch | |
| 2008/0034502 A1 | 2/2008 | Copeland | |
| 2008/0172791 A1 | 7/2008 | Walczyk | |
| 2008/0301878 A1 | 12/2008 | Elhabashy | |
| 2011/0048428 A1 | 3/2011 | Hunter, Jr. | |
| 2012/0103344 A1 | 5/2012 | Hunter, Jr. | |

* cited by examiner

*Primary Examiner* — Ophelia A Hawthorne
(74) *Attorney, Agent, or Firm* — Waller Lansden Dortch & Davis, LLP; Matthew C. Cox

(57) ABSTRACT

A device for stabilizing a patient's arm during a surgical procedure including a base configured to fit on an operating table. A support arm has a proximal end attached to the base and a distal end extending away from the base. A cuff is mounted on the distal end of the support arm to support the wrist of a patient. One or more bicep pads are connected to the support arm and are positioned to fit about the bicep of a patient lying on an operating table.

13 Claims, 6 Drawing Sheets

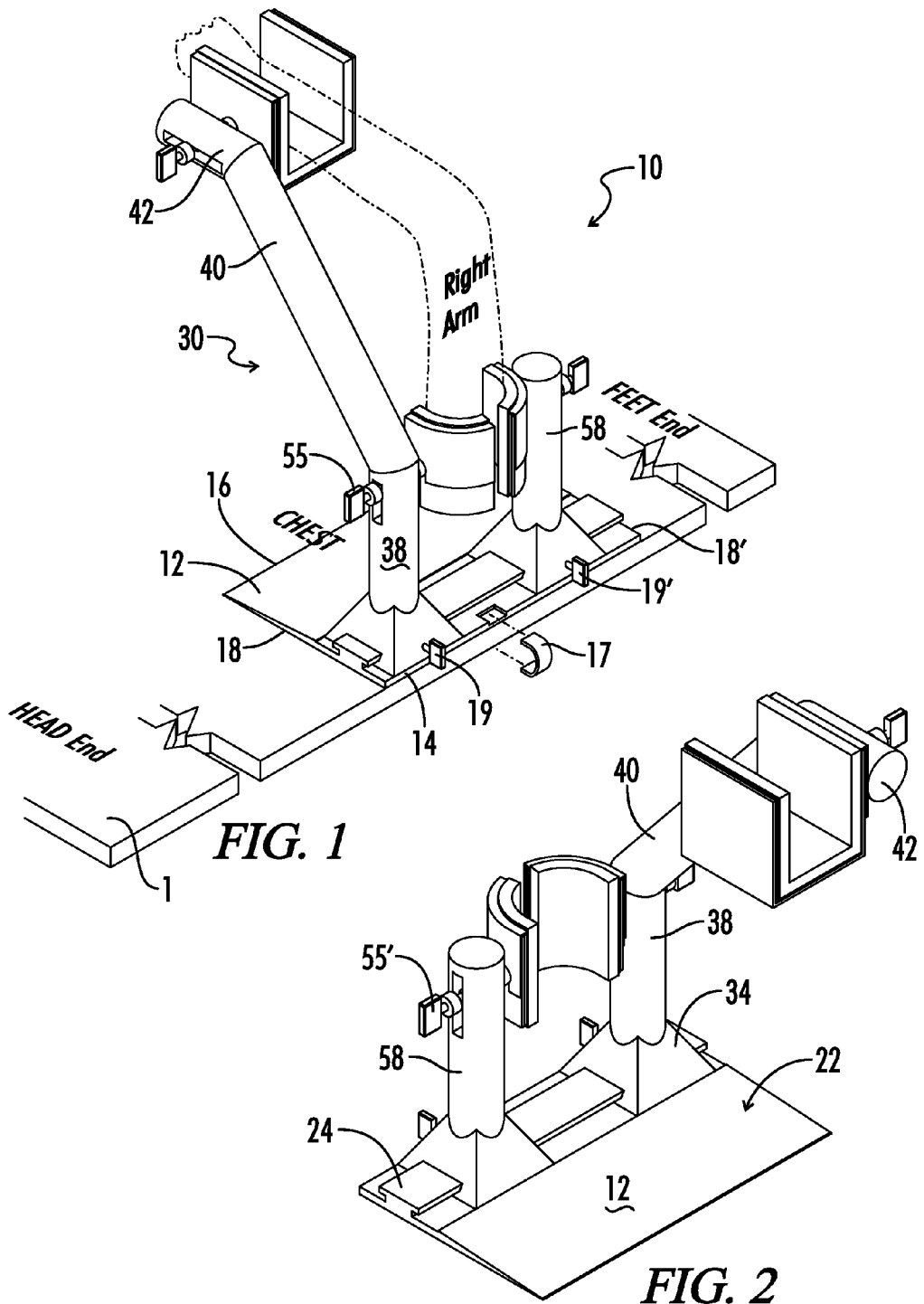

9,408,768 B1

ARM STABILIZER FOR ELBOW SURGICAL PROCEDURE

CROSS-REFERENCES TO RELATED APPLICATIONS

This application is a Continuation of U.S. patent application Ser. No. 12/550,701 filed Aug. 31, 2009, now U.S. Pat. No. 8,230,864, entitled Arm Stabilizer for Elbow Surgical Procedure, all of which is hereby incorporated by reference in its entirety.

BACKGROUND

The present invention relates generally to a surgical accessory product, more particularly to an arm stabilizer for use in conjunction with an elbow surgery procedure.

Surgical procedures on the extremities of humans occur with great frequency, and particularly surgeries on the arm, elbow, and hand. Injuries to a person's arm, elbow, and hand come frequently from falls, reaching to catch one's self, slipping and landing on an elbow causing a shattering of the bone structure within the elbow, and attempting to brace oneself in response to a fall resulting in fractured bones in the humerus, elbow, forearm, and hand.

During the course of surgical procedures to repair the broken bones in the arm, historically the patient's arm has been placed on a pillow or some other support structure resting on the patient's waist or chest, or a foam pad can be used to support the arm. This procedure fails to properly secure and maintain in a fixed position the extremity on which the procedure is being conducted. There have been numerous attempts to address this problem, including those described and illustrated in U.S. Pat. No. 473,200, 5,785,057, 7,017, 215, 7,143,458, 7,441,293, and U.S. Publication No. 2008/0301878. The prior devices that are available in the industry, including those described in the aforesaid patents are an improvement over the simple use of a pillow resting on the patient's chest, but remain inadequate. Specifically, the prior art products fail to provide good exposure to the extremity, particularly to the patient's elbow, and make it difficult for the surgeon and nurse assistants to have easy, unfettered access to the patient's elbow, to properly complete the surgical procedure.

BRIEF SUMMARY

The present invention addresses the problems associated with the prior art devices designed to provide stabilization to a patient's arm during a surgical procedure by providing a simple, adjustable, steady support for a patient's arm, fully exposing the patient's elbow to both the doctor and nurse assistants in order to make access to the elbow convenient, open, and easy to perform the surgery. The invention consists of an arm stabilizer including a stabilizer base that is designed to sit on the operating table with a proximal edge contiguous with the edge of the operating table and the base extending on the operating table and tapered so that it may rest beneath the patient lying on the operating table. The proximal edge of the base is clipped or otherwise secured and attached to the operating table.

Along the topside of the base is a rail having the cross sectional shape of the tongue of a tongue and groove joint. This rail allows or facilitates the mounting of a support arm on the base. The support arm can be mounted on the base via a groove in the foundation of the support arm and is adjustable laterally along the length of the rail to the proper position proximate the patient. The support arm also extends away from the proximal edge of the base with a cuff support extending from the distal end of the support arm to hold a cuff on which the patient's wrist would rest. The cuff of the present invention includes a foam section that is comfortable to the wrist of the patient and a backing that fits into a cuff basket, all of which are mounted onto the cuff support.

The portion of the support arm directly adjacent the base is a vertical spacer and that spacer faces a standard, or support post, that also has a post foundation with a grooved slot mating with the tongue of the rail. With the groove in the foundation of the support arm and standard, and utilitarian set screws, the standard and spacer can be adjusted back and forth relative to each other and ultimately fixed in place by tightening the set screws.

Attached to the spacer and standard are bicep pads using pad supports and those bicep pads fit around the patient's biceps to stabilize that portion of the patient's arm, leaving the portion above the bicep, including the elbow, positioned freely and openingly facing the surgeon with the patient's wrist in the cuff. The positioning of the standard allows the tightness around the bicep of the patient to be adjusted and the device can be easily adjusted to fit any size bicep and hold that portion of the arm in a vertical position with the forearm extending away from the patient, resting in the cuff, and clearly exposing the elbow to the surgeon and the nurse for the surgical procedure.

BRIEF DESCRIPTION OF THE DRAWINGS

FIG. 1 illustrates in perspective view an embodiment of the arm stabilizer of the present invention.

FIG. 2 shows a perspective view of the invention from the opposite side of FIG. 1.

DETAILED DESCRIPTION

Figure 3:
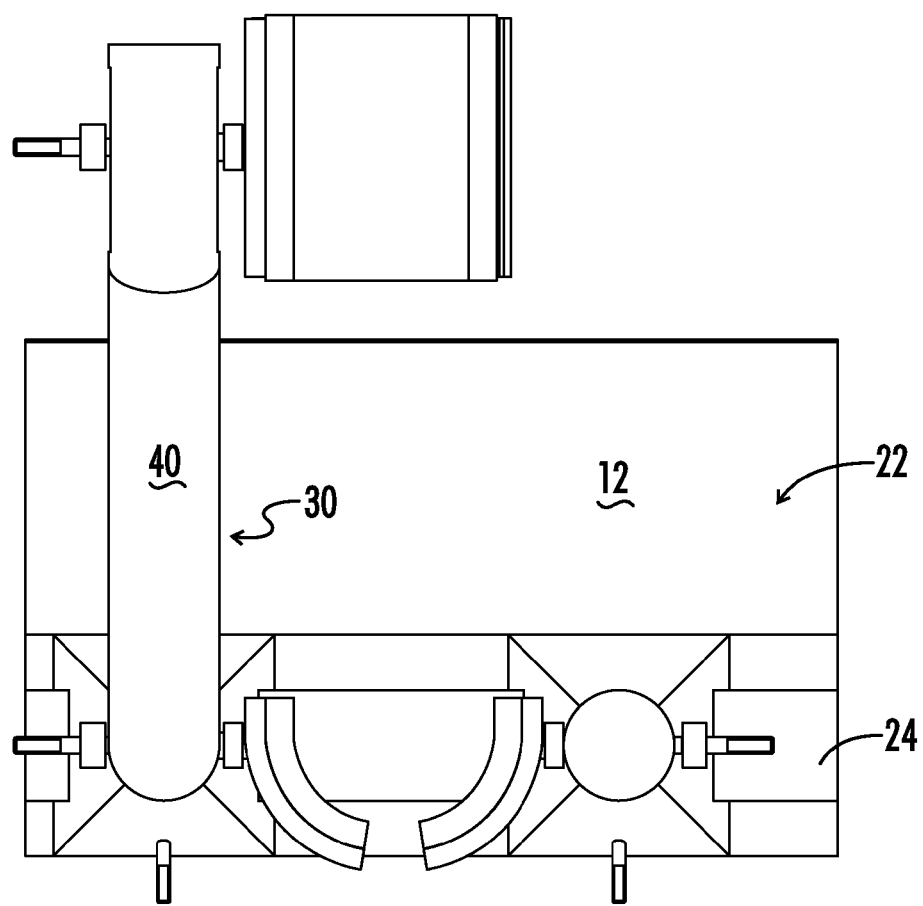
FIG. 3 shows a top view of the invention.
Figures 4, 5:
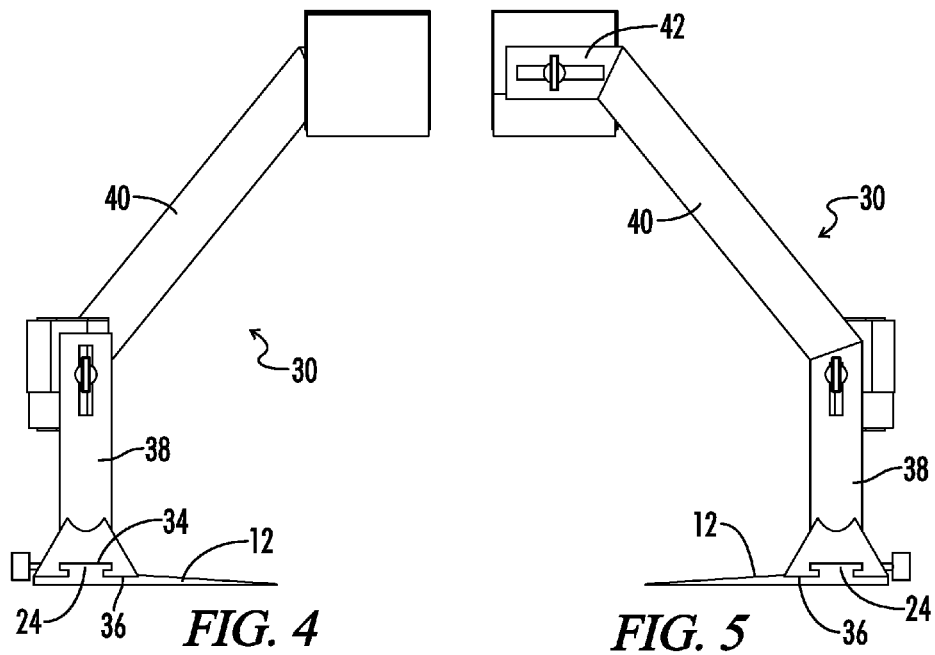
FIG. 4 shows a view from the feet end of the operating table.
FIG. 5 shows a view of the invention from the head end of the operating table.
Figures 6, 7:
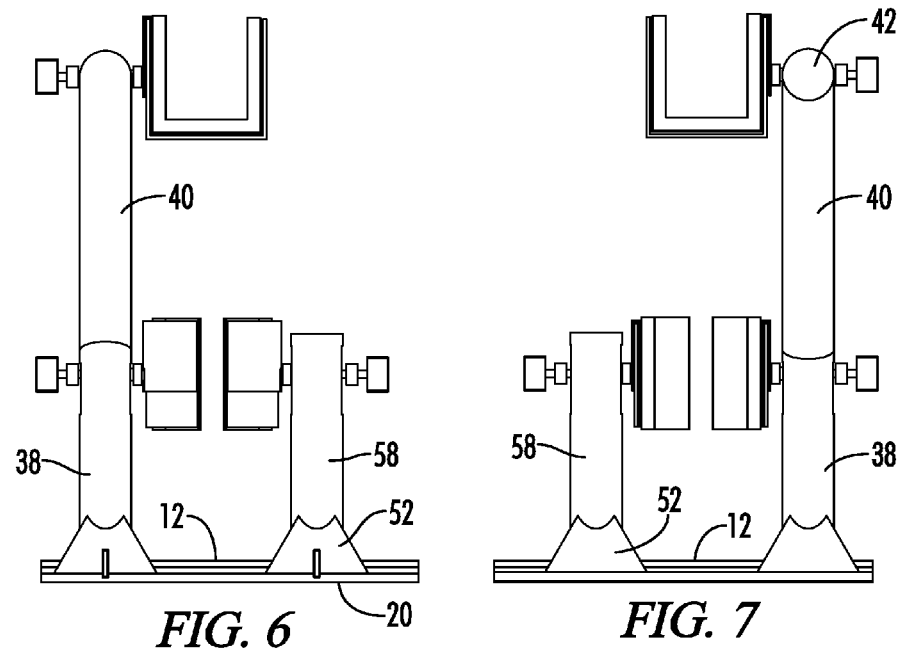
FIG. 6 shows a view of the invention from the doctor's side of the table.
FIG. 7 shows a view from the patient's side of the table.

Described herein and illustrated in the drawings attached is an embodiment of the invention that best illustrates the invention as claimed. This embodiment is designed to rest on an operating table 1 and includes an arm stabilizer 10, including a stabilizer base 12 having a proximal edge 14 and a distal edge 16. There are opposite ends 18, 18', a bottom 20, and a top 22. Extended laterally along the top of the base 12 is a rail 24 having a generally T-shaped cross-section, somewhat akin to the shape of the tongue of a tongue and groove joint. Of course, other equivalent shapes would be readily recognized by those of ordinary skill in the art that would be effective for the same purposes as the shape as illustrated in the drawings.

The arm stabilizer further includes an arm 30, having a foundation 32, or arm foundation, with a first groove 34 in the bottom of the foundation 32. The first groove 34 extends through the length of the arm foundation 32 and is of a shape to match the shape of the cross-section of the rail 24. The first groove 34 is in the arm foundation bottom 36 such that the base can slip over the rail and fit securely, but adjustably, on the rail 24.

Extending up from the arm foundation 32 is a spacer section 38. The spacer section 38 is shown in tubular shape but could be of any shape or form that generally spaces the arm stabilizer up from the foundation and provides open access to the elbow of the patient. The spacer section 38 extends generally vertically upwardly from the base but of course could have some angular or curved component.

Connected to the upper end of the spacer section 38 is an extension 40 that extends angularly in a direction that, when the groove 34 of the foundation 32 is slid onto the tongue 24 of the stabilizer base 12, the extension 40 extends generally perpendicular to the length of the rail 24. Extending from the distal end of the extension 40 is a cuff support 42 which extends substantially horizontally away from the proximal edge 14 of the stabilizer base 12.

Attached to the cuff support is a cuff basket 64. The cuff basket 64 is generally U-shaped and includes a cuff basket mounting spindle 70 which extends through a cuff support slot 72 in the cuff support 42 and can be securely attached thereto by a wing nut 74. Fitted within the cuff basket 64 is a cuff backing 62 which has fitted within it a foam cuff 60. The cuff backing 62 has a U-shape that matches substantially the cuff basket and nests within the cuff basket. The cuff backing 62 also has a U-shape lip that fits over the panel of the cuff basket on which the mounting spindle is attached and a notch 68 fits over the cuff basket mounting spindle 70 so as to securely hold the cuff backing in place inside the cuff basket 64. The foam cuff 60 is generally frictionally mounted within the cuff backing 62 and may be glued to the cuff backing.

The purpose for having a cuff basket along with a foam cuff held by a cuff backing is that the cuff/cuff backing combination may be disposable. The remainder of the device, consisting of base plate and support arms may be used over and over again and can be sterilized by steam autoclave or other technique. The cuff and/or cuff backing and bicep pads are replaced at each sterile application with a sterile replacement product. Alternatively, the entire cuff basket assembly and bicep pads assembly could be disposable.

Figure 8:
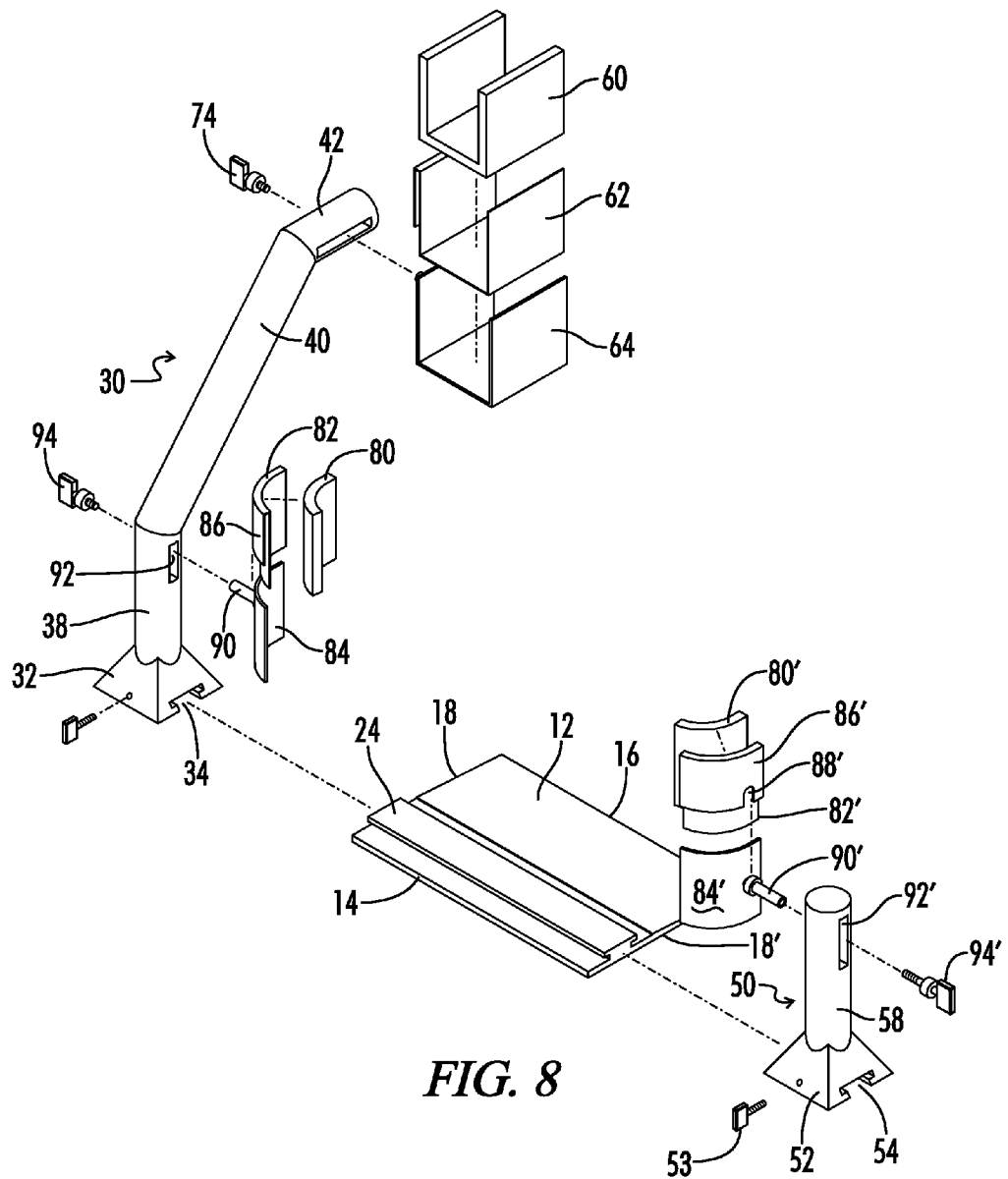
FIG. 8 shows an exploded perspective view of the invention.
Figure 9:
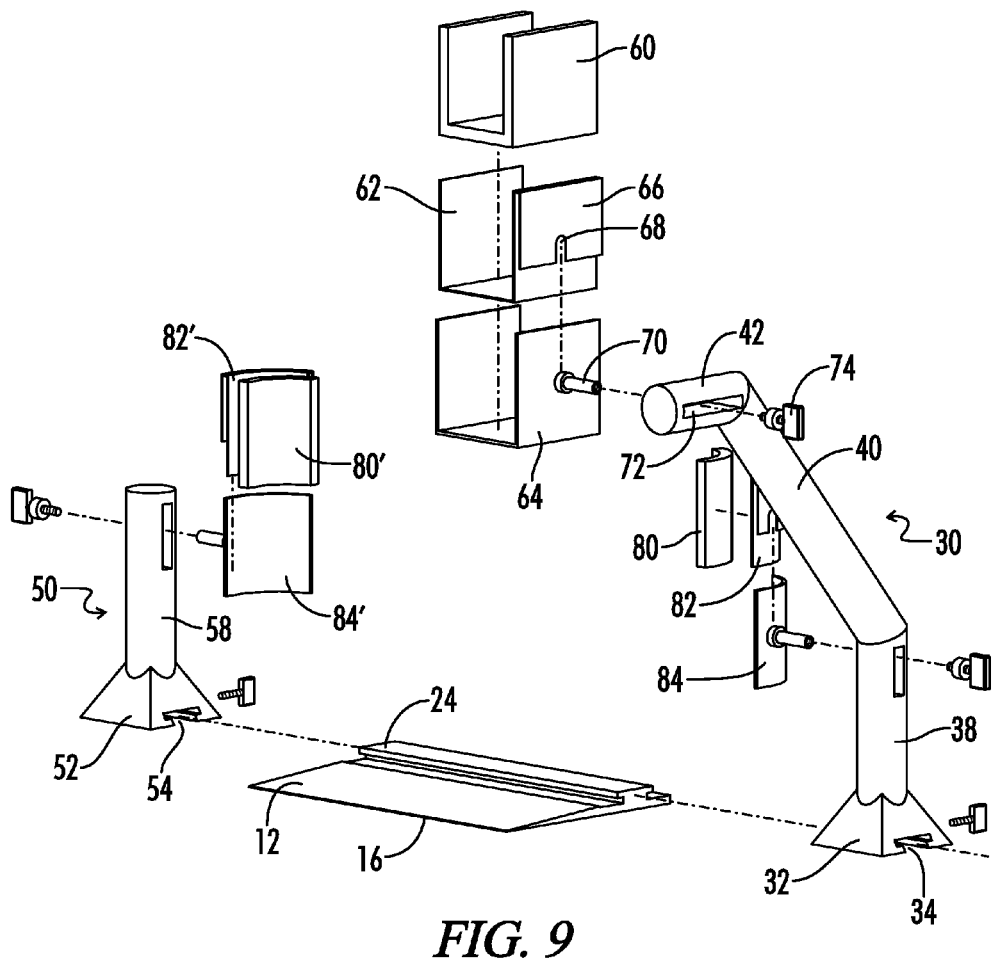
FIG. 9 shows an exploded perspective view of an embodiment of the invention from the patient's side.
Figures 10, 11:
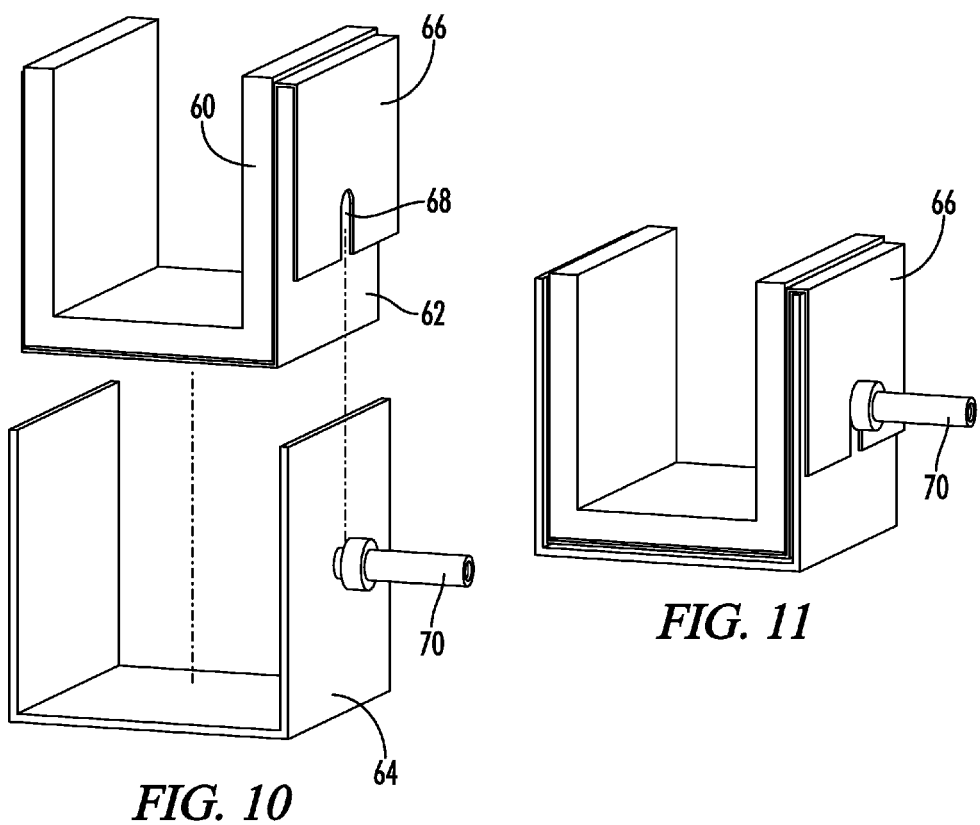
FIG. 10 shows an exploded view of the cuff and cuff holder.
FIG. 11 shows a perspective view of the assembled cuff.

As can be seen from FIG. 1 and FIGS. 8 and 9, the cuff basket 64 can be adjusted to move toward or away from the proximal edge of the stabilizer base 12 to make it comfortable for the wrist of the patient when the patient is lying on the operating table and has his arm in the device. Generally the hospital or surgery center will carry different sizes of the foam cuff 60 so that a cuff can be selected to conform to the size of the wrist of the patient and a snug fit can be achieved with the wrist of the patient fit tightly within the foam cuff 60 and held without any binding or movement. The interchangeability of the cuff through the system provided is a convenient feature to make the device universally applicable regardless of the size of the patient.

Referring to FIGS. 8 and 9, the humerus/bicep pad and support can be best seen. Included in the device is a support post 58, or standard, having a post foundation 52 with a second groove 54 in the bottom of the post foundation. The second groove 54 is of a shape identical to the shape of the first groove 34 in the foundation of the support arm and likewise, the post foundation 52 can be mounted on the rail 24 and adjusted axially along that rail and locked in place by a set screw 53. The support post extends up from the base similar to the way the spacer section 38 extends up from the arm foundation.

A spacer slot 92 extends through the spacer 38 and standard 58 has a standard slot 92'. The spacer slot 92 is designed to receive the first pad support mounting spindle 90 and likewise, standard slot 92' is designed to receive the second pad support mounting spindle 90'. The slots 92, 92' run vertically along the axis of the spacer 38 and the standard 58 so that the first and second pad supports 84, 84' can be adjusted vertically and tightened into a fixed position by set screws 94, 94'. Pad backings 82, 82' are provided to fit over the first and second pad supports 84, 84' much in the same way as the cuff backing 62 fits over the cuff basket 64. The pad backings include lips 86, 86', and a pad backing notches 88, 88' that slips over the pad supports 84, 84' and the first and second pad support mounting spindles 90, 90'.

Glued to or otherwise attached to the pad backings 82, 82' are the first and second humerus/bicep pads 80, 80'. These pads are foam and generally disposable and are designed to hold the bicep of the patient in the manner shown in FIG. 1. Alternatively, the entire pad support assemblies could be disposable. The support post 50 can be moved laterally to come closer to or farther away from the spacer 38 to adjust the tightness of the bicep pads about the bicep of the patient to provide comfort and stability.

In practice, the invention can be assembled and placed on the operating table with the proximal edge 14 of the base extending coterminously along the proximal edge of the operating table. The base can be clipped onto the table with a clip 17 to hold it in place. When assembled on the operating table in this fashion, the rail 24 with a T-shaped cross section runs substantially parallel to the length of the proximal edge 14. The arm foundation 32 is then mounted onto the base 12 by sliding the first groove 34 over the rail 24 and fixed in position by tightening a wing nut/set screw 19. Next, the height of the bicep pad 84 is adjusted to fit the patient's bicep and tighten down with a wing nut 55.

The cuff basket 64 is then connected to the cuff support 42 by placing the mounting spindle 70 through the slot 72 and tightening the device fixedly to the cuff support by the wing nut 74. Of course the position of the cuff basket 64 can be adjusted to be closer to the surgeon or farther away from the surgeon by virtue of the length of the slot 72, and once the device is positioned to a comfortable resting place for the wrist of the patient, it is tightened securely. Next, the cuff backing 62 with the foam cuff 60 in place is placed in the cuff basket 64 to receive the wrist of the patient.

The final step of the stabilization is to place the support post 50 on the base 12 by sliding the second groove 54 over the rail 24. The pad support 84' is then placed in position by passing the mounting spindle 90' through the slot 92' and tightening the same with the wing nut 94'. The pad backing 82', which serves as the carrier for the bicep pad 80', is mounted over the pad support 84' into a secure position. As can be seen from the drawings, the pad supports 84, 84' along with the pad backing 82, 82', and pads 80, 80' themselves are arcuate shaped to fit about the bicep of the patient.

The next step of the process is to slide the support post 50 along the rail 24 to a point where pad is tight against the patient's bicep so that the patient's bicep is securely fitted between pads 80, 80' to hold the bicep sturdy and the arm in a fixed position. The arm is now stably maintained with the pads being adjustably mounted so that they can be placed to accommodate a patient having any sized arm. The arm extends upright and is bent at the elbow to place the wrist in the cuff 60 and rest comfortably there. The elbow is exposed openly and directly adjacent the edge of the operating table so that the surgeon can have full access to the elbow to conduct any elbow operation surgery procedure that might be necessary. In addition, the physician's assistant can have immediate and unfettered access to the patient's arm, the arm is held stable and in position, but fully exposed up and away from the patient's body to allow appropriate bed cloths to be placed over the patient and likewise the opportunity to keep the patients arm clean and extended from the patient's body.

The fully enabled embodiment of the invention illustrated in the drawings has been described in detail and with specificity. However, it would be understood that a number of variations could be embodied within the description. For example, the cuff can be generally squared off as shown in the drawings or curved; the cuff could be tubular or it could have a channel of length as if shown in the drawings; the cuff could be of a variety of combinations of metal, plastic, and foam; the cuff assembly could include a cuff basket designed to receive a foam cuff that is connected to the basket either by friction, by screws, by adhesives, by Velcro®, by slot and groove combinations, and other readily known methods of connecting products made of similar materials. The cuff backing could be plastic, metal or a hard foam, the cuff could connect to the cuff backing by any number of variable combinations that are well known such as adhesives, screws, clips, Velcro®, and the like. Likewise, the support arm and standard can be of a variety of shapes. As illustrated in the drawings, the shape of both the support arm and the standard is that of a pipe. Generally, that pipe could be of any cross section such as hexagonal, octagonal, elliptical or the like, or that cross section could be square or rectangular. Any known cross section could be considered so long as the shape of the support arm and standard is such that it is not so large as to interfere with exposing the elbow of the patient to the physician for ready access during the surgical procedure. The support arm is shown as extending up vertically and then at an angle to expose the elbow of the patient when the patient is prepared for surgery. However, that shape of the support arm could be curved, have multiple angles, or even a generally directional angle of extension up from the base without curves or bends, the objective being to position the cuff at a point away from the surgeon and above the patient's body to give the most open access to the patient's elbow. Further, the preferred embodiment description shows both the support arm and standard as moveable along the rail and moveable relative to each other. Alternatively, one or the other of the support arm and standard could be fixed and the other of the support arm and standard could be moveable relative to the rail which would easily enable the bicep pads to be adjusted, one relative to the other, to engage about the bicep of the patient. Also, the bicep pads could be moveable relative to stationary support arm and standard. All of these various embodiments are considered to be within the scope of one or more of the claims appended hereto.

Thus, although there have been described particular embodiments of the present invention of a new and useful it is not intended that such references be construed as limitations upon the scope of this invention except as set forth in the following claims.

What is claimed is:

1. An apparatus for simultaneously supporting both a patient's humerus and the patient's wrist during a surgical procedure on the patient's elbow when the patient is lying supine on an operating table, comprising:
    a base configured to be detachably secured to the operating table;
    a support arm extending upwardly from the base, the support arm including a proximal end attached to the base and a distal end extending upwardly away from the base;
    a wrist support pad attached to the distal end of the support arm, wherein the wrist support pad is positioned to receive the patient's wrist, the wrist support pad being moveable relative to the support arm; and
    a bicep pad attached to the support arm, the bicep pad being positioned to support the patient's humerus when the patient's wrist is positioned on the wrist support pad,
    wherein the bicep pad is positioned on the support arm between the proximal end of the support arm attached to the base and the wrist support pad.

2. The apparatus of claim 1, further comprising a pad support mounted on the support arm, wherein the bicep pad is disposed on the pad support.

3. The apparatus of claim 2, wherein the pad support is moveable relative to the support arm.

4. The apparatus of claim 3, further comprising a wrist support mounted on the support arm, wherein the wrist support pad is disposed on the wrist support.

5. The apparatus of claim 4, wherein the wrist support is moveable relative to the support arm.

6. The apparatus of claim 5, wherein the wrist support pad comprises a foam material.

7. The apparatus of claim 6, wherein the bicep pad comprises a foam material.

8. The apparatus of claim 1, further comprising a wrist support mounted on the support arm, wherein the wrist support pad is disposed on the wrist support.

9. The apparatus of claim 8, wherein the wrist support is moveable relative to the support arm.

10. The apparatus of claim 1, wherein the wrist support pad comprises a foam material.

11. The apparatus of claim 1, wherein the wrist support pad includes a U-shape.

12. A device for stabilizing a patient's arm by supporting the patient's humerus and the patient's wrist on the patient's arm during a surgical procedure, comprising:
    a base configured to fit on an operating table;
    a support arm extending upwardly from the base, the support arm including a distal end extending away from the base;
    a first pad support attached to the support arm;
    a first bicep pad attached to the first pad support, wherein the first bicep pad is positioned to support the patient's humerus when the patient is located on the operating table in a supine position such that the patient's arm extends upwardly from the operating table;
    a wrist support attached to the distal end of the support arm; and
    a detachable wrist support pad disposed on the wrist support, wherein the wrist support pad is positioned to support the patient's wrist when the patient's humerus is supported by the first bicep pad,
    wherein the first pad support is attached to the support arm at a location between the wrist support and the base.

13. The device of 12, further comprising:
    a clip configured to detachably secure the base to the operating table.

* * * * *